(12) United States Patent
Blendinger (10) Patent No.: US 10,672,125 B2
(45) Date of Patent: Jun. 2, 2020

(54) METHOD AND SYSTEM FOR SUPPORTING MEDICAL PERSONNEL

(71) Applicant: Siemens Healthcare GmbH, Erlangen (DE)

(72) Inventor: Heinz Blendinger, Aisc (DE)

(73) Assignee: Siemens Healthcare GmbH, Erlangen (DE)

( * ) Notice: Subject to any disclaimer, the term of this patent is extended or adjusted under 35 U.S.C. 154(b) by 109 days.

(21) Appl. No.: 16/057,671

(22) Filed: Aug. 7, 2018

(65) Prior Publication Data
US 2019/0050984 A1 Feb. 14, 2019

(30) Foreign Application Priority Data
Aug. 8, 2017 (EP) ..................................... 17185322

(51) Int. Cl.
*G06T 7/00* (2017.01)
*A61B 90/00* (2016.01)
(Continued)

(52) U.S. Cl.
CPC ............. *G06T 7/0012* (2013.01); *A61B 34/10* (2016.02); *A61B 34/20* (2016.02); *A61B 90/37* (2016.02);
(Continued)

(58) Field of Classification Search
CPC .................................................. G06T 7/0012; G06T 7/70; G06T 7/62; A61B 90/37; A61B 34/20; A61B 34/10;
(Continued)

(56) References Cited

U.S. PATENT DOCUMENTS 9,775,681 B2 * 10/2017 Quaid .................... A61B 34/37
2005/0288578 A1   12/2005 Durlak
(Continued)

FOREIGN PATENT DOCUMENTS

DE   102004030836 A1   1/2006
DE   102012224057 A1   6/2014

OTHER PUBLICATIONS

European Search Report for corresponding Application No. 17185322. 9-1126, dated Feb. 16, 2018.
(Continued)

*Primary Examiner* — Asghar H Bilgrami
(74) *Attorney, Agent, or Firm* — Lempia Summerfield Katz LLC (57) ABSTRACT

A method and a system for supporting medical personnel in a procedure on a patient are provided. Medical image data of the patient and of a medical object is continuously captured. Using the image data, a digital patient model is generated and continuously updated, and a position of the medical object is continuously tracked. Through automatic processing of the image data, a situational and/or spatial context in which the medical object is situated is determined. Based on the determined context from the patient model, speech data that describes at least part of the determined context in speech form is automatically generated. The speech data is then output to the medical personnel by an acoustic speech output and/or as text on a display surface. Thus, the medical personnel may be informed particularly reliably and with little distraction about the respective current situation.

15 Claims, 2 Drawing Sheets

(51) Int. Cl.
    *G16H 10/65* (2018.01)
    *A61B 34/20* (2016.01)
    *G16H 40/63* (2018.01)
    *G16H 50/50* (2018.01)
    *G16H 30/40* (2018.01)
    *A61B 34/10* (2016.01)
    *G06T 7/62* (2017.01)
    *G06T 7/70* (2017.01)
    *G06K 9/00* (2006.01)
    *G10L 13/04* (2013.01)
    *A61B 17/00* (2006.01)

(52) U.S. Cl.
    CPC ..... *G06K 9/00362* (2013.01); *G06K 9/00771* (2013.01); *G06T 7/62* (2017.01); *G06T 7/70* (2017.01); *G10L 13/043* (2013.01); *G16H 30/40* (2018.01); *G16H 40/63* (2018.01); *G16H 50/50* (2018.01); *A61B 90/361* (2016.02); *A61B 2017/00115* (2013.01); *A61B 2034/104* (2016.02); *A61B 2034/105* (2016.02); *A61B 2034/2051* (2016.02); *A61B 2034/2057* (2016.02); *A61B 2034/2065* (2016.02); *A61B 2090/376* (2016.02); *G06K 2209/057* (2013.01); *G06T 2207/30021* (2013.01); *G06T 2207/30101* (2013.01)

(58) Field of Classification Search
    CPC ........ A61B 90/361; A61B 2017/00115; A61B 2034/2065; A61B 2090/376; G16H 30/40; G16H 50/50; G16H 40/63; G10L 13/043; G06K 9/00771; G06K 9/00362
    See application file for complete search history.

(56) References Cited

U.S. PATENT DOCUMENTS

| | | |
|---|---|---|
| 2008/0137923 A1 | 6/2008 | Spahn |
| 2016/0120608 A1* | 5/2016 | Essenreiter ............ A61B 90/37 600/410 |
| 2016/0191887 A1 | 6/2016 | Casas |
| 2018/0235715 A1* | 8/2018 | Amiot .................... A61B 34/10 |
| 2019/0015163 A1* | 1/2019 | Abhari .................... G06T 7/70 |

OTHER PUBLICATIONS

Lee, Jun.-Goo, et al. "Deep learning in medical imaging: general overview." Korean journal of radiology 18.4 (2017): 570-584.

* cited by examiner

METHOD AND SYSTEM FOR SUPPORTING MEDICAL PERSONNEL

This application claims the benefit of EP17185322.9, filed on Aug. 8, 2017, which is hereby incorporated by reference in its entirety.

BACKGROUND

The present embodiments relate to supporting medical personnel in a procedure on a patient.

Nowadays, efforts are made to carry out both diagnostic as well as interventional procedures with the least possible injury to the individual patient. During an interventional procedure in the surgical field (e.g., during a minimally invasive intervention by a catheter), usually a surgeon or physician who is active (e.g., performing the procedure) is informed by an image representation on a monitor about a respective current status of the intervention. For this purpose, for example, a continuous image capture of an intervention region may be provided by an X-ray device. It can be disadvantageous herein that the surgeon must actively turn his gaze away from the real situation (e.g., the catheter, his hands, and the patient) and direct his gave to the monitor in order to correlate the real externally visible situation and his movements in the guidance of the catheter with the internal situation displayed on the monitor (e.g., the position of the catheter tip). Further, medical personnel present may often inform themselves of the current status and progress of the procedure only insufficiently or inexactly by observing the image representation. Persons who are not familiar with the manner of the image representation and/or may not see the monitor must often be informed by other persons in an error-prone manner. For example, this may involve an additional and disadvantageous burdening of the respective active physician, in addition to his work of placing the catheter that is critical to the wellbeing of the patient, to inform or instruct the medical personnel present. An adaptation of the position of the monitor so that the monitor is more easily visible to more personnel may lead to a suboptimal visibility or legibility of the monitor for the active physician, which is also considered disadvantageous.

SUMMARY AND DESCRIPTION

The scope of the present invention is defined solely by the appended claims and is not affected to any degree by the statements within this summary.

The present embodiments may obviate one or more of the drawbacks or limitations in the related art. For example, an improved progress of medical procedures by supporting medical personnel is provided.

A method for supporting medical personnel in a procedure or in an intervention on a patient includes a plurality of method acts. Initially and during the procedure, image data of the patient and of a medical object generated by a medical imaging method is continuously captured. From the image data or using the image data, a digital patient model (e.g., a model of the patient) is generated and continuously updated. A respective current position of the medical object is continuously tracked. This may take place based on the image data. Also as part of the method, a situational and/or spatial context in which the medical object is found is determined by automatic processing of the image data by an image processing algorithm. Based on the determined context, from the patient model (e.g., using or proceeding from or based on the patient model), speech data is automatically generated. This speech data describes at least a part of the determined context (e.g., the respective situation in speech form). The automatically generated speech data is then output to the medical personnel. This outputting takes place by an acoustic speech output and/or as text on a display surface.

The method may be used in many medical procedures and interventions. Accordingly, the medical object may also be created or configured in a wide variety of different ways. Without restricting the present embodiments thereto, the method may be used in a diagnostic or interventional minimally invasive use of a catheter. The medical object may thus be, for example, the catheter or a part thereof. Similarly, the medical object may, however, be a surgical or generally a medical instrument, an implant, a vessel support (stent), a tool, a screw, a wire, a tube, and/or the like. Finally, the medical object may be capturable by the imaging method (e.g., able to be made visible).

In the context of the present embodiments, the continuous capture of the image data may relate both to a recording or generation of the image data (e.g., an imaging of the patient) or to a recalling or reading-out of the image data (e.g., from an imaging generating device or a data store). The fact that the image data is captured continuously does not have to imply an uninterrupted operation in the context of the present embodiments, but may provide a regular, repeated capture of image data. For example, a series of X-ray images may be recorded at a particular frequency. The image data is thus not captured at just one time point, but at a plurality of time points in a temporal sequence. The image data may thus form, for example, a temporal sequence or a temporal development.

The image data items may each image or represent a subregion of the patient and/or of the medical object. In order to generate the image data, different imaging methods may be used herein. Thus, the image data may be, for example, X-ray, ultrasonic, angiographic, or tomographic images. Equally, the image data may be two-dimensional or three-dimensional or include a series of 2-D or 3-D images.

The patient model may be an image of at least one subregion of the patient and of the also imaged medical object reconstructed based on the image data or of raw data. Since both at least a subregion of the patient and also of the medical object are contained in the image data and/or imaged, the patient model also includes an imaging or representation of at least a part of the patient and of the medical object. Thus, the patient model may also represent or describe a spatial positional relationship between at least one part of the patient and the medical object. The patient model may be a three-dimensional model. Similarly, the patient model may be dynamic (e.g., may model, image, and/or describe a movement, such as a relative movement, of the patient, a part of the patient and/or of the medical object). Thus, the patient model may model (e.g., take into account and/or illustrate) a heart or breathing movement of the patient and/or an advancing of the catheter in the patient.

The patient model may thus be an entirely or partially visual representation. The patient model may contain a supporting visualization or illustration. This may be an automatically or manually generated marking, emphasizing, coloration, labeling or the like. It may be possible, for example, to represent the movement of the medical object or a path of the medical object overlaid on the image data in order to achieve a better recognizability or evaluability.

In the context of the present embodiments, the patient model may also be or include a mathematical and/or graphical description or modeling of at least one subregion of the patient and of the medical object. In one embodiment, the medical object (e.g., type or model of the medical object) may be identified. Then, for example, a CAD model of the medical object may be recalled from a corresponding model database and processed or included in or for the patient model. This may be, for example, a part of the patient model describing the patient generated from the image data, and then, the virtual model of the medical object may be overlaid on this part. The respective current position of the medical object may also be determined from the image data. The patient model may thus be constructed based on different data sources. By this, the patient model may be precise, and a simple automatic further processing and evaluation of the patient model may be enabled.

In general, by the use of the patient model, a bundling of all the available relevant data and information may also be achieved in the patient model. On updating the model, the respective current image data (e.g., the respective last recorded X-ray image) may be incorporated into the patient model. Herein, for example, a part of the patient that has not yet been imaged and only schematically modeled in the patient model may be replaced by the real X-ray image that is then available. Similarly, for example, an image quality of the patient model may be improved by taking account of the respective current image data in that the respective current image data is used, for example, to improve a noise suppression (e.g., combined with the image data already cumulatively captured up to the respective current time point). The patient model also enables a particularly flexible evaluation of all the captured data. Thus, for example, the visualization and/or the evaluation is not restricted to the conventionally, often common fleeting live representation, since the captured image data and possibly further data or information is used in the patient model and thus is not, apart from a live reproduction, discarded unused.

The tracking of the position of the medical object may take place, for example, using a position transmitter on the medical object itself and/or by an image evaluation or image processing of the image data. This may be facilitated by markings or markers that may be arranged on the medical object. The manner of these markings or markers may be dependent on the imaging method used so that it is provided in each case that the markings or markers may be captured and/or imaged (e.g., represented) by the respective imaging method. Similarly, manual information or input for tracking the position of the medical object may also be captured and processed or evaluated. Thus, for example, the medical personnel may manually specify or input that the medical object has achieved a specific position or orientation. By this, for example, the automatic image evaluation for tracking the position of the medical object may be supported or provided in that reliable reference points are created. Thus, a plausibility check of the automatic evaluation or position determination is enabled.

The context in which the medical object is situated may be characterized or given by different data and/or situations. The spatial context may specify, for example, at which position or site the medical object is found (e.g., relative to and/or in or on the patient). Thus, for example, a different context may be provided according to whether the medical object (e.g., the catheter) is situated in a leg, in the chest cavity, in a particular vessel, or on a particular organ of the patient. The spatial context may also be determined by a position of an entry site of the catheter in the patient and/or a movement direction relative to (e.g., on or in) the patient. Thus, for example, in each case, a different context may be provided depending on whether the medical object is moved in the patient from beneath upwardly, from above downwardly, into, or out of the patient.

Similarly, the spatial and/or situational context may be characterized or specified by a spatial position or body posture of the patient, by an orientation or position in which an imaging device (e.g., the X-ray device) is situated or has been situated at a respective recording time point of the image data, or by an environment of the patient (e.g., depending on whether the patient is situated in an operating room (OP), in an outpatient or precarious treatment situation or environment, or the like).

The situational context may be specified or characterized, for example, by the type of the respective currently performed procedure, the type of medical object, a status of the patient (e.g., a respective medical and/or anatomical situation or peculiarity), or the like.

The determination or taking into account of the context may enable a particularly precise, appropriate, and reliable automatic evaluation that is suited or adapted to the situation and thus enables a correspondingly advantageous reliable and appropriate determination of the speech data that is to be created.

The context may be determined, for example, automatically by evaluating the image data, the patient model, and/or further data or data sources. Thus, for example, a digital patient record may be read out or evaluated automatically in order to determine particular physical features of the patient and/or the type of procedure.

The image processing algorithm may, for example, include or carry out a segmentation, an edge or object recognition, a movement recognition, and the like. It may therefore be automatically determined where the medical object is situated in the patient (e.g., at what spacing from a particular body part or anatomical feature of the patient the medical object is situated). This may be sufficient as the context. In one embodiment, a more detailed context may additionally supply the information as to where a respective target point or a respective target position of the medical object is (e.g., in or on the patient), whether the respective procedure provides for a pure movement of the medical object or a manipulation on the patient, and/or whether the medical object moves according to a pre-determined or ideal shape or path.

In order to determine the context, the patient model may therefore be used or evaluated, for example, to determine the relative position of the medical object in relation to the patient. Herein, the determined context may make this factual information evaluable and/or classifiable in a content-related or transparent framework.

The speech data may thus describe the respective current situation (e.g., the respective current relative position of the medical object) in a generally comprehensible, clear form. The speech data may use clear speech expressions or words, so that the speech data thus does not amount, for example, to no more than abstract specifications of coordinates or numbers. The speech data may be created, for example, in the form of sentences or sentence fragments (e.g., in natural speech or the speech form). In actual examples, the expressions or information "36 mm in front of Arteria Renalis" may be used as speech data, for example, to specify the current position of a catheter tip, "another 23 mm to the valve plane" may be used in order, for example, to specify the current position and movement direction of the catheter tip relative to a concrete automatically recognized or previously defined reference point (e.g., such as a heart valve), "center of the stent reached" may be used in order to describe a relation, for example, of the catheter tip to another object, or "current vessel diameter 12 mm" may be used in order to characterize the situation or a current environment (e.g., of the catheter tip or to describe an anatomical feature or detail of the patient; in an environment of the medical object). In the generation of the speech data, apart from the determined context and the patient model, further data, control signals, configurations, or settings may also be taken into account.

For the acoustic speech output of the speech data, the speech data may be converted, for example, by a speech synthesis or text-to-speech (TTS) method, into audio signals. These may then be transferred, for example, to an output device that may include, for example, a loudspeaker. The acoustic speech output enables the entire medical personnel to be informed, regardless of the respective standpoint or the visibility of a particular region, for example, of a particular screen. Thus, the active physician or surgeon (e.g., the medic carrying out the procedure) is relieved of this responsibility, which may contribute to a patient benefit and a smooth and improved sequence of the procedure. Due to the timely and reliable informing of the medical personnel, the medical personnel may adapt to the respective situation, prepare for the impending events, and direct attention (e.g., visual attention) to respective relevant regions or objects. By this, therefore, the sequence of the entire procedure and an organization and interaction, for example, in the operating room may be improved.

For the active physician, it is advantageous that the physician may use the speech data output as feedback and/or for estimating or evaluating the respective situation. For intellectual uptake of the information conveyed by the acoustically output speech data, the active physician does not need to avert his gaze from the patient, a device operated by the physician, or the physician's hands. By this, the physician may carry out the procedure interruption-free, particularly rapidly, and safely. Since the output speech data or the corresponding information contained therein is determined by automatic evaluation or processing of the patient model, the output speech data may be more precise or more reliable than an estimate by the respectively active physician or other medical personnel, based only on experience or observation of X-ray images or the like. During the procedure, typically there is neither time nor personnel available, for example, to measure a respective spacing manually in the X-ray images, so that the present embodiments may also provide data that conventionally was often not available during the procedure.

The output of the speech data as text on a display surface may serve, for example, to support the acoustic speech output or as a reference for backup, for example, in the event that a person has not reliably understood the acoustic speech output. However, the output of the speech data exclusively as text may also be advantageous. Thus, through the purely text-based output, an acoustic distraction may be prevented, and simultaneously, the output of the precise automatically determined model-based data may be enabled.

Technically, the output of the speech data may be realized both in acoustic form and also in visual form in different ways. For example, an output via a room loudspeaker is equally as possible as an output via respective individual headphones of the medical personnel. Herein, for example, an individualization of the respectively output speech data may also be provided. This provides that, for example, dependent upon a respective task of each person, each person receives only a relevant selection matched to him (e.g., a subset) of all the speech data generated or available (e.g., as relevant to his respective task). This is enabled or facilitated by the automatic generation of the speech data, since an automatic categorization and allocation may be undertaken particularly rapidly. The output of the speech data as text may take place, for example, in the form of a log book, for example, on a separate screen, or in a separate display region of the display surface. By this, a history that is a sequence of the procedure may be followed at any time. The text may, for example, be inserted as subtitles to the respective image data. The text may be output in a moving stream as continuous text, comparable to a news ticker. By this, a size of a display region needed for displaying is advantageously minimized, and it is thereby provided that the most current speech data is always displayed.

In an embodiment, as the context or as part of the context, an imaged subregion of the patient and/or an anatomical feature of the patient and/or a spatial-geometric relation between the medical object and at least one environment detail in an environment of the medical object is determined. The spatial-geometric relation may be, for example, a spacing of the medical object from a pre-determined and/or automatically recognized anatomical feature of the patient. In other words, it may therefore be determined (e.g., automatically) which subregion of the patient is represented in the image data (e.g., a leg, a lower or upper torso region, an arm, or the head of the patient). This may be achieved by evaluating the image data and/or by taking account of or evaluating further data sources. Thus, for example, an access to a database may also take place similarly to a capture or reading out of a user input undertaken manually, for example, by the medical personnel and/or an evaluation of geometry data. The geometry data may describe or define, for example, a location of the patient and/or of the device generating the image data (e.g., therefore, a particular arrangement and orientation of the patient in a C-arm X-ray device). The determination of the subregion of the patient that is represented enables a restriction and specifying of the possibilities regarding which anatomical details particular features of the image data may be concerned. Based on the respective geometry, it may, for example, be precluded that particular parts of the patient are represented in the respective image data, so that a more reliable identification is enabled. By this, the automatic object recognition may be improved.

The anatomical feature of the patient may be, for example, a particular anatomical detail in the region of the medical object, such that the precise placement or localization of the medical object is simplified. By the determination of the anatomical feature, this may advantageously be mentioned in the speech data in order to enable the medical personnel to make an improved and simplified classification of the speech data output or of the respective current situation since, by this, the situation may be described particularly clearly. Similarly, the anatomical feature may be a particular individual configuration of a body part, of an anatomical detail, or, for example, a particular injury to the patient. By this, for example, a possible movement play for the medical object or a deviation from a normal state may be determined. This may then be taken into account in the automatic identification of individual features in the image data and/or in the generation of the speech data. Similarly, based thereon, for example, a particular target sequence of the procedure may be selected as a reference from the database, and/or a prepared target sequence of the procedure may be modified taking account of or dependent upon the anatomical feature. Advantageously, this may enable a precisioning of the speech data or of the information conveyed thereby, similarly to, for example, an automatic warning to the medical personnel.

By the determination of the spatial-geometric relation between the medical object and the at least one environmental detail, which may be, for example, the anatomical feature or another anatomical feature, the medical personnel may be informed, particularly in the event of a movement of the medical object, regarding the relative position of the medical object, which is often not or only barely recognizable from outside, without attention having to be diverted from the medical object itself and/or from the patient. This may be advantageous in order to prevent an unintended injury to the patient by the medical object.

In a further embodiment, the context or a part of the context is determined by an anatomical comparison of the image data and/or of the patient model with a provided anatomical database. In other words, in order to determine the context, a comparison of the image data and/or of the patient model or of a respective part thereof with, for example, example images or model data stored in the anatomical database or an anatomical catalog or atlas may thus be carried out. Herein, for example, a simple difference formation, a threshold value method, a pattern recognition, or a similarly analysis or similarity assessment may be carried out. This may be realized, for example, by a conventional image processing algorithm or, for example, by a neural network. The context may thus be determined entirely or partially automatically, so that an effort for manual operation actions may be minimized, as may an error proneness.

In a further embodiment, geometry data is used in order to generate the patient model and/or to determine the context, a location of the patient, and/or an environment of the patient (e.g., a relative position of a patient couch and/or of a device generating the image data). This may also enable a more reliable automatic determination or identification of the procedure carried out, just like an automatic determination or prediction of an expected position or an expected sequence of one or more anatomical features of the patient. For example, a course and/or a diameter of a vessel or a form of an organ may change dependent upon the position of the patient, according to whether the patient is in a prone, supine, or a side position. Similarly, taking account of the geometry data may be used for more exact and more reliable identification of the imaged subregion of the patient or of anatomical details or features imaged or represented in the image data. For example, through evaluation of the relative location or position of the device generating the image data (e.g., the X-ray device and/or of the location of the patient and/or of the patient couch), a number of possibilities for which anatomical features may be represented by the image data may be reduced or restricted. Similarly, for example, based on the geometry data, a restricted subregion of the anatomy database that is taken into account for the automatic comparison of the image data for determining the context may be specified. Overall, through taking account and/or use of the geometry data, a more exact and more reliable and/or detailed determination of the context may be enabled, and a more exact patient model may be generated.

The geometry data may be obtained, for example, by the capture and reading-out of a user input, by calling a respective current status of the device generating the image data, and/or by processing and evaluating sensor data. The sensor data may be captured and/or provided, for example, by location, position, acceleration, or movement sensors, image capturing sensors, by a laser scanner, and/or the like.

In a development, the patient and/or an environment of the patient are spatially captured by a 3-D camera. Corresponding camera data provided by the 3-D camera is then processed to generate the patient model and/or to determine the context. In other words, for example, the location or posture of the patient may be spatially captured by the 3-D camera. This enables the patient model to be generated particularly rapidly and true to life, which enables a particularly precise description of the respective situation by the speech data. Through the capture of the environment of the patient and a corresponding evaluation of the corresponding camera data, it may be determined (e.g., automatically) in which room or which type of room the patient is situated, which devices are used at which time point in the procedure, and/or which persons of the medical personnel are present and/or participating in the procedure. It may thus be possible, for example, using an image processing of the camera data to determine automatically a relative position or a relative location of the patient relative to the device generating the image data (e.g., the X-ray device). This may enable the represented subregion of the patient to be identified automatically. For this purpose, the camera data may be converted, for example, into the aforementioned geometric data.

In a further embodiment, the medical object is identified by an automatic object recognition algorithm and/or by an automatic comparison of the image data with a provided object database. Object data assigned to the identified object is then recalled from the object database or another database and processed to generate the patient model and/or to determine the context. In other words, therefore, it may be determined automatically not only where the medical object is situated, but what type of medical object or which medical object it is. For example, the medical object may be identified with regard to type or with regard to specific model. Through the identification of the medical object, for example, a more precise modeling of the medical object and/or interaction of the medical object with the patient may be enabled.

Similarly, the identification of the medical object may be used in order, for example, to determine the type of procedure and/or a target behavior of the medical object. If, for example, the medical object is identified as a catheter, then it corresponds to an expected behavior or target behavior that the catheter moves in a vessel of the patient. This may be used to generate the speech data particularly precisely and particularly reliably, so that the speech data describes the respective situation appropriately. In addition, the object data that may define, for example, a precise shape and size of the medical object and an exact position of markings or markers on the medical object, for example, relative to an endpoint may also contribute thereto. If, for example, only the position of the marker or markers or markings of the medical object may be automatically determined based on the image data, then from this, taking account of the recalled object data, precisely, for example, one current position of a tip or an end point of the medical object may be calculated, since the object data may include the location of the marker as readily as the exact size and shape of the medical object. This precise specification may then be output in the form of the speech data.

In a further embodiment, a catheter is used as the medical object. While the catheter is passed through a vessel of the patient, a diameter of the vessel at a respective current position of the catheter (e.g., a tip of the catheter) is automatically determined by an image processing algorithm. The respective diameter may then be output as part of the speech data. Similarly, the determined diameter may be used as an input variable or a calculation basis for determining one or more other variables, for characterizing the position of the medical object, or the like. These may then be described or stated when the speech data is generated, for example, therefore through the speech data. For example, it may be calculated and stated automatically that the catheter tip has reached a portion of the vessel the diameter of which is smaller or larger than the catheter or its diameter. The diameter of the vessel may be determined, for example, continuously or in regular stated temporal and/or spatial intervals.

In the speech data, the specified vessel diameter may be output or stated, for example, in pre-determined temporal intervals, respectively, after the catheter has completed a pre-determined route or distance in the vessel and/or if the diameter of the vessel has changed by a pre-defined absolute or relative value (e.g., against a pre-defined value, a particular measurement value, or a mean value) and/or if the diameter of the vessel falls below or exceeds a pre-defined threshold value. By this, a number of detail data or individual data given or output by the speech data may be reduced. At the same time, the medical personnel at respective relevant sites are informed about the diameter of the vessel. By the automatic determination of the cross-sectional dimension of the vessel (e.g., the vessel diameter), the medical personnel is relieved of determining the vessel diameter manually.

The determined values of the vessel diameter may be stored. From this, a profile of the respective vessel is generated. The profile may represent a useful reference. It may also be possible to use this profile as a basis for an automatic diagnosis or evaluation of a condition of the patient. Through the automatic determination of the vessel diameter, in a practicable manner and with negligible cost in time and computation, a plurality of measurement values of the vessel diameter may be determined, so that a significantly more exact profile may be generated than by a manual measurement.

In order to determine the vessel diameter automatically, the catheter may be used as a reference. For example, a line or length that extends perpendicularly to a main extent direction of the catheter through the catheter tip and meets or intersects a wall of the vessel at two mutually opposite points may be generated or calculated. The vessel diameter may then simply be determined as the length of the stretch or line between their points of intersection with the vessel wall. The vessel diameter may serve the medical personnel, for example, as an important variable in order to be able to assess or estimate the position of the catheter. For example, by following or specifying the vessel diameter indications precisely, a start, middle, and/or end point of a stenosis may be determined, and the catheter may be placed accordingly precisely. Similarly, based on the vessel diameter, for example, a vessel branching may be recognized and/or the medical personnel may be notified that particular care is required if, for example, the vessel diameter is particularly small (e.g., falling beneath a defined threshold value, since in such a case, a movement of the catheter may particularly easily lead to damaging of the vessel). In such cases, the automatic determination of the vessel diameter may be advantageous, just as the automatic speech output of the corresponding value (e.g., also if due to a respective image quality of the image data, the vessel diameter is not clearly and reliably determinable or recognizable by the medical personnel themselves with a brief glance). A relatively long interruption of the movement of the catheter in order, for example, to study the image data extensively may increase an injury risk, which may be prevented by the present embodiments.

In a further embodiment, on continuous capture of the image data between two documentation images of the patient (e.g., for documentation purposes), a plurality of fluoroscopic images is recorded with reduced radiation intensity. These fluoroscopic images are then processed for updating the patient model. In other words, the documentation images are thus recorded or generated at a first radiation intensity, and the fluoroscopic images are recorded at a second radiation intensity. The second radiation intensity is lower than the first radiation intensity. By this process, due to the higher radiation intensity, the documentation images depict or record relevant details, key positions, or key time points during the procedure as precisely and recognizably as possible. At the same time, the patient may be represented or imaged continuously during the procedure, where a burdening of the patient is minimized with the reduced radiation intensity for the fluoroscopic images. The documentation images and the fluoroscopic images are part of the image data.

The reduced radiation intensity may lead for each individual fluoroscopic image to a reduced image quality. This may, however, be compensated for in that the patient model is based cumulatively on all the image data captured up to the respective current time point (e.g., the documentation images and the fluoroscopic images). Due to the particularly large and constantly growing database for the patient model despite the reduced radiation intensity for the fluoroscopic images, for example, as compared with each individual fluoroscopic image, a reduced noise level or an improved signal-to-noise ratio and therefore an improved image quality may be achieved. This process of recording the fluoroscopic images at reduced radiation intensity is also based on the recognition that during significant temporal portions of the procedure, a maximum image quality is not necessarily needed for the successful performance of the procedure. In the context of the method of the present embodiments, this process may be applied since through the automatic image evaluation and the automatic tracking of the medical object, the medical object may be accurately located or localized despite the reduced radiation intensity and a reduced image quality possibly associated therewith. This is based thereon that a suitable image processing algorithm may often recognize object edges faster and more accurately than is reliably possible for a human observer, particularly while the human observer is simultaneously occupied with other tasks during the performance of the procedure on the patient.

The reduced radiation intensity is also less important in the present method for the successful performance of the procedure as compared with conventional methods since, due to the output of the speech data describing the respective situation, the medical personnel do not have to rely on visual recognition and on their own interpretation of the image data. Thus, the process proposed herein may therefore reduce the radiation burden for the patient without endangering the success of the procedure. It is therefore a particular advantage of the present embodiments not to dispose of the fluoroscopic images or the data and information contained therein that are continuously captured during the procedure at reduced radiation intensity, but to use (e.g., evaluate or process) the fluoroscopic images for continuous updating and/or improvement of the patient model and thus for generating the most accurate and reliable possible spoken description through the speech data.

In a further embodiment, different speech data is generated and classified into different categories dependent upon content. These different categories may relate, for example, to an anatomic feature or the medical object or a spatial and/or temporal relation. Then, only speech data from selected categories is output. The fact that different speech data is generated provides that a plurality of different facts, states, conditions, situations or the like are captured or determined or evaluated and described separately from one another through respective speech data (e.g., expressed or verbalized). Thus, a speech data item may be, for example, a position indication of the medical object (e.g., "catheter tip 5 mm before marked heart valve plane"). A second speech data item different therefrom may state, for example, the vessel diameter at the current position of the catheter tip. These two speech data items are thus different, independent of one another, and relate to different facts or different types of fact. Consequently, these two speech data items are therefore classified into different categories or allocated to different categories. If, for example, the medical personnel now make the selection that only speech data of the category "anatomical feature" should be output, according to one or more of the present embodiments and the method, only the second speech data item would be output, since this describes or states an anatomical feature (e.g., the vessel diameter).

The classification or allocation of the speech data to the different categories thus takes place dependent upon a type of the respective speech data item or dependent upon a theme or a condition and/or a reference or reference object of the respective speech data item. In order to be able to classify the different speech data into the different categories, for example, the respective characteristics or features of the image data or of the patient model that is used or taken into account on generation of the respective speech data or underlie the respective speech data or to which reference is made through the respective speech data items, are identified. If, for example, by the image processing algorithm, a spacing between two edges is determined, then the objects to which the edges belong or which are delimited by the edges are identified (e.g., as the catheter and a vessel or organ wall). Then, an automatic tagging or an automatic comparison with a specified allocation table may be provided, where the spacing information or the speech data item based thereon is classified dependent upon which objects have been identified or which key words have been assigned, into one or more relevant categories.

In one embodiment, different, specialized image processing algorithms or subalgorithms or subroutines may be provided for determining different facts or different types of facts. Thus, for example, a first algorithm for determining the vessel diameter and a second algorithm for determining a spacing between the medical object and a particular marking and/or a particular anatomical feature may be provided, etc. Since the different algorithms then therefore always capture or determine or evaluate different facts or situations, for each of the algorithms, an automatic classification of output data issued thereby may be provided into a particular pre-determined category. By this, a particularly exact and reliable categorization may be enabled.

The selection of the categories or speech data to be output may be undertaken by a user input or a corresponding configuration. It may similarly also be possible, for example, dependent upon the type of procedure, upon a respective current stage of the procedure, upon the respective current position of the medical object and/or other factors, to make an automatic selection. By this, at any time point, for example, only speech data that is particularly relevant for the success of the procedure is output, so that the medical personnel are not overburdened by too large a quantity of output speech data. Since the output of the speech data (e.g., in the case of an acoustic speech output) also occupies some time, it can be provided by the selection that no waiting time or a waiting queue for generated but not yet output speech data arises. Thus, for example, when the medical object has approached to a pre-determined spacing from a particular anatomical feature (e.g., a heart valve), the respective current spacing or a corresponding timely output may be more important than the respective current vessel diameter or a current speed of the medical object, so that then automatically only the category for the reproduction of the corresponding speech data that relates to a spatial relationship between the medical object and the patient or a particular anatomical feature (e.g., the spacing) is selected. Thus, for example, it may be reliably prevented that an injury to the patient occurs through an unintended contact with the medical object (e.g., a perforation of a wall or membrane).

The image processing algorithm or another imaging processing algorithm may be configured to recognize a movement and/or a speed (e.g., relative to the patient). Dependent upon the movement or the speed, an automatic selection of the speech data to be output may be undertaken, and/or the output of the speech data may be dispensed with at least temporarily (e.g., for a pre-determined time period). As a result, for example, at a speed lying above a pre-determined threshold value, it may be prevented that due to the time required for generating and for outputting the speech data, a time offset (e.g., lag) arises, so that the speech data output at a particular time point would not describe the respective situation at the actual position that the medical object occupies at this time point. Thus, for example, it may be prevented that a particular spacing or vessel diameter is stated if this is no longer current at the time point of the corresponding speech output because the medical object has already moved significantly more than a pre-set threshold value compared with a position at which the spacing or the vessel diameter or the like was determined. If the speed of the medical object subsequently falls again below the corresponding threshold value, then the output of the speech data may be automatically continued or started again. While the medical object has moved, speech data generated may then be skipped (e.g., not output).

In a further embodiment, the image data and/or the patient models of a plurality of different patients are processed by a method of machine learning (e.g., by a neural network), and thereby, a normal state and/or a normal behavior of at least a part of the patient is learned. Such a normal state may relate to or describe, for example, a vessel diameter or a movement scope of a heart valve or the like. Based on the learned normal state and/or the learned normal behavior, a deviation between the respective current image data and/or the respective current patient model on one side and the normal state and/or the normal behavior on the other side is then recognized or determined. Speech data describing the deviation is then generated and output. Alternatively or additionally, the respective current image data and/or the respective current patient model is stored in a deviation database. Thus, the medical personnel may be notified of recognized deviations that may be difficult to recognize, for example, depending on the scaling or the extract of corresponding image data displayed on a screen. The deviation database may therefore be understood as a self-learning library. This may serve, for example, as a reference and/or for automatic diagnosis or evaluation of symptoms, abnormalities, and deformities, or the like. The recognized deviation and/or the deviation database may be used for determining the context and/or for generating and/or for updating the patient model. By this, the speech data output may describe the actual situation (e.g., the reality) accurately and reliably.

A system of one or more of the present embodiments for supporting medical personnel in a procedure on a patient has a capture device, a data processing device, a speech synthesis device, and an output device. The capture device serves or is configured for continuous capture of image data of the patient and of a medical object generated by a medical imaging method. The data processing device serves or is configured for continuously updating a digital patient model based on the respective current image data. The data processing device further serves or is further configured for tracking a position of the medical object and for automatic determination of a situational and/or spatial context in which the medical object is situated, by processing the image data using an image processing algorithm. The data processing device may also be configured for generating the digital patient model, for example, based on the image data and/or other data or data sources. The speech synthesis device serves or is configured to generate speech data based on the determined context from the patient model, where the speech data describes at least part of the determined context in speech form. The output device serves or is configured to output the speech data to the medical personnel by an acoustic speech output and/or as text on a display surface of the output device.

The system of one or more of the present embodiments may be configured, for example, to carry out at least one embodiment of the method. For this purpose, the system may have, for example, a data carrier with a program code that represents or encodes the method acts of the method. The system may have at least one microchip or microprocessing device that may carry out this program code. The system may also include one or more interfaces and/or at least one user interface, by which data and/or input may be received or captured.

The properties and developments of the method of one or more of the present embodiments and the corresponding advantages set out above and below are each analogously transferable to the system and/or to components and devices used or usable for carrying out the method, and vice versa. Such developments of the method and of the system that have embodiments not explicitly described here in the respective combination thus also belong to the present embodiments.

DETAILED DESCRIPTION

The components of the exemplary embodiments are each individual features of the invention and are also to be considered independently of one another. The components further develop the invention independently of one another and are thus also to be considered individually, or in a different combination from that shown, as a constituent of the invention. The embodiments described are also enhanceable through other of the previously described features of the invention.

Figure 1:
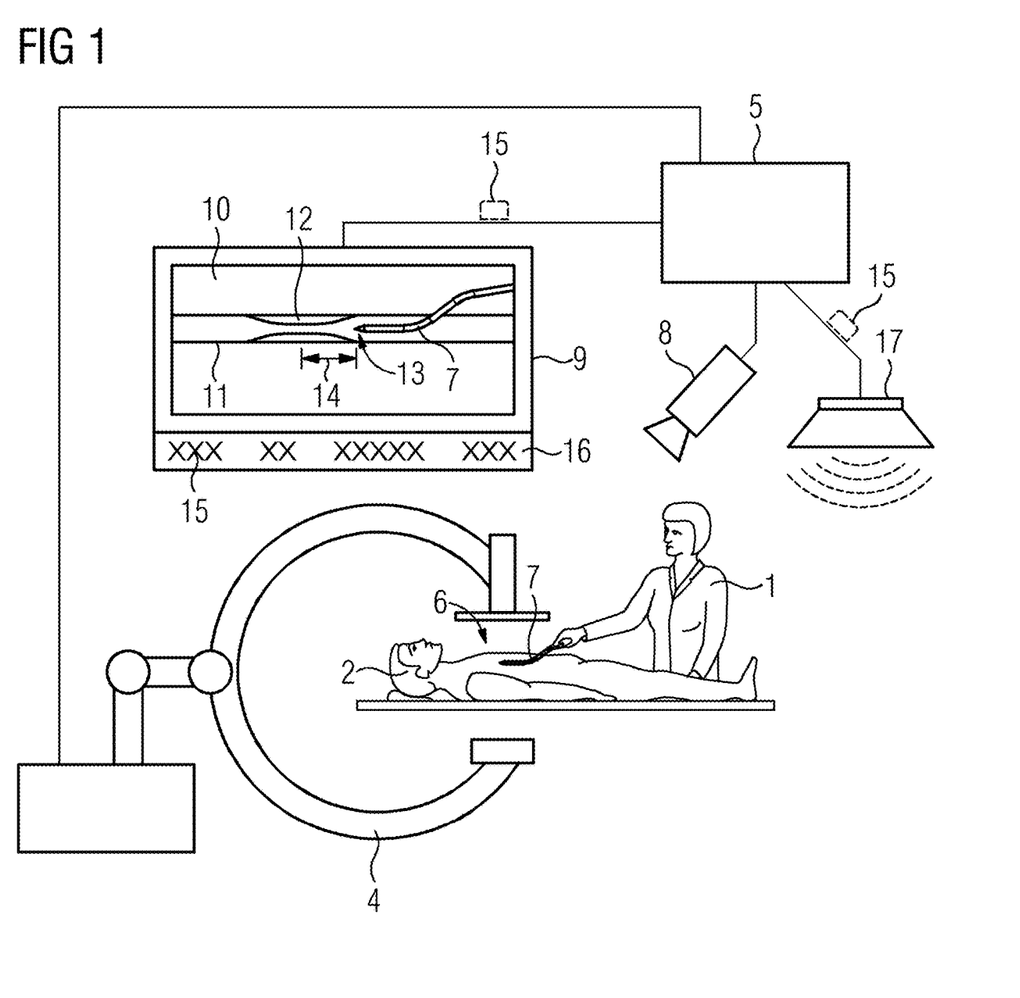
FIG. 1 shows a schematic representation of a surgical situation in which a physician is supported by a system.
Figure 2:
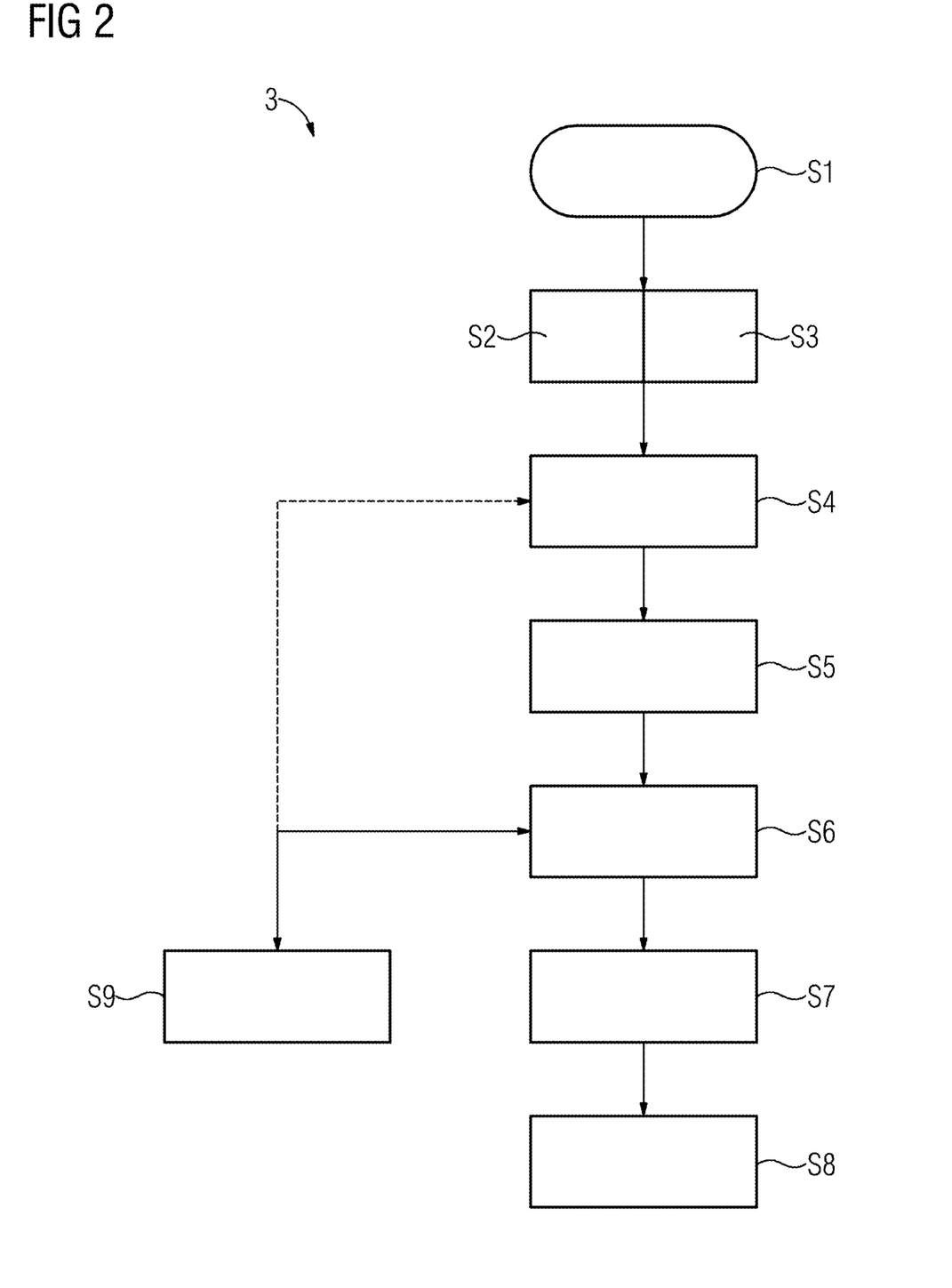
FIG. 2 shows an exemplary schematic sequence plan of a method for supporting medical personnel in a procedure on a patient.

FIG. 1 shows schematically a situation in an operating room in which medical personnel (e.g., an active physician 1) is supported by a system in performing a procedure on a patient 2. FIG. 2 shows an exemplary schematic sequence plan 3 of a corresponding method for supporting medical personnel (e.g., the physician 1). In the following, FIG. 1 and FIG. 2 are described jointly.

In a method act S1, the method is started. Preparatory measures may be performed or may already have been performed. In this case, this may include a positioning of the patient 2 in or on a C-arm X-ray device 4. Similarly, for example, before the start of the actual medical procedure on the patient 2, data usable for the further method may be provided to a data processing device 5 that carries out the method. Thus, for example, data relating to the patient 2, such as age, height, weight, sex, and the like, is input into the data processing device 5 or is recalled by the data processing device 5 from the electronic patient record of the patient 2. Similarly, for example, a type and/or a planned sequence of the procedure to be carried out may be specified or input. From these and/or further data, using the data processing device 5, a preliminary digital patient model of the patient 2 may be generated. Similarly, such a preliminary patient model of the patient 2 may be provided pre-prepared to the data processing device 5.

In a method act S2, using the X-ray device 4, at least a subregion of the patient 2 is generated or captured in a medical imaging method. In the example shown, a chest region 6 of the patient 2 is imaged. In the present case, the actual medical procedure in which the physician 1 introduces a medical object (e.g., a catheter 7) into the patient 2 begins therewith. As soon as the catheter 7 reaches the chest region 6, therefore, both the patient and also at least a subregion of the catheter 7 are imaged by the X-ray device 4. In the course of the subsequent method acts also, at least during the medical procedure, image data of the patient 2 and of the catheter 7 may be recorded and/or generated continuously by the X-ray device 4.

At the same time, in a method act S3, further data may be captured by suitable sensors. In the present case, for this, the patient 2 and an environment of the patient 2 is captured in images by a camera 8 that is, for example, configured as a 3-D camera. The camera 8 may also capture, for example, the C-arm of the X-ray device 4. The camera may be activated, for example, automatically together with the X-ray device 4 or with the data processing device 5. Camera data generated by the camera 8 that may thus image a respective subregion of the patient 2, of the X-ray device 4, and an environment of the patient 2 is transferred via a corresponding data connection to the data processing device 5.

In a method act S4, the data processing device 5 may capture the image data of the patient 2 and of the catheter 7 generated by the X-ray device 4 and, making use of this image data, may create a patient model of the patient 2. The patient model may be generated anew at this time point or, for example, generated by further processing or updating the preliminary patient model. For the generation of the patient model, data possibly previously provided may also be used, just as the camera data delivered by the camera 8 may. The camera data may herein be converted, for example, in an intermediate step, into geometric data that defines relative locations, orientations, or positions of the patient 2, the X-ray device 4, and/or, for example, the physician 1. Further medical objects (e.g., a clamp or an endoprosthesis) may be captured and recognized or identified. Such further objects may then also be represented or modeled in the patient model. Similarly, during the procedure (e.g., at one or more time points), a contrast medium may be administered to the patient 2, and thus, a vascular tree (e.g., a pattern of blood vessels of the patient 2) may be made visible. Such data (e.g., the shape of the blood vessels) may also be entered into the patient model by the data processing device 5. Since new image data is continuously supplied by the X-ray device 4 and/or the camera 8, the data processing device 5 may also update the patient model continuously based on the respective most up-to-date available data.

In order to facilitate the processing of the image data, the camera data, and/or further data provided, relevant information regarding the respective data source may be provided to the data processing device 5 manually or automatically. Thus, the data processing device 5 may, for example, automatically recognize from which, or which type of, data source respective data or a respective data stream (e.g., the image data or the camera data) originates. Similarly, data regarding, for example, further medical objects already in or on the patient 2 (e.g., a vessel support (stent) or the like) may be provided to the data processing device 5. Such data may then also enter the patient model.

The patient model may thus bundle all the available data.

The data processing device 5 may process and evaluate the image data, for example, using an image processing algorithm. Thus, for example, the image data may be segmented, and/or objects (e.g., the catheter 7) may be recognized automatically. As soon as the catheter 7 has been recognized, a position of the catheter 7 is continuously tracked in a method act S5. The tracking is maintained or carried out for as long as the catheter is captured and recognized. The catheter or the position of the catheter may thus also be tracked during the subsequent method acts.

Since, therefore, absolute and/or relative position changes and/or movements of at least the catheter 7 are captured and/or recognized and correspondingly represented in the patient model, the patient model may also serve as or be designated a navigation map at least for a subregion of the patient 2.

In order to provide a sufficient accuracy, the position of the catheter 7 and/or the patient model may be updated, for example, at a frequency of at least 10 Hz.

The respective current image data and/or the respective current patient model may be displayed or represented, for example, by a display device 9 in a first display region 10 of the display device 9. In this case, a portion of the vessel 11 of the patient 2 is represented. In the present example, the vessel 11 has a stenosis 12. Also located in the vessel 11 is the catheter 7, where a catheter tip 13 of the catheter 7 (e.g., a front end region) faces toward the stenosis 12. During the procedure, the catheter 7 may be moved by the physician 1, for example, toward the stenosis 12.

In a method act S6, the data processing device 5 processes at least the image data at least by the image processing algorithm or another image processing algorithm in order to determine a situational and/or spatial context in which the catheter 7 is situated at the current time point. In order to determine this context, more of the available data may also be used or taken into account. This may concern, for example, information regarding the procedure, further medical objects, the patient, and the like. Provided it has not previously occurred to generate the patient model, in the determination of or in order to determine the context, for example, at least one anatomical detail and/or a spatial relationship may be determined. Thus, for example, by a pattern recognition and/or a comparison of the image data with a corresponding anatomical database, the vessel 11 may be identified and/or the stenosis 12 can be recognized as such. Similarly, for example, a current spacing 14, indicated schematically, from the catheter tip 13 to the stenosis 12 or a marked or automatically calculated center point of the stenosis 12 may be determined and/or calculated. Similarly, for example, a respective current diameter of the vessel 11 at the level of the catheter tip 13 may be determined and/or calculated.

In one embodiment, the physician 1 or other medical personnel may undertake a marking. Thus, for example, a particular position or a particular anatomical feature or detail may be marked, and/or a planned path for the catheter 7 or the like may be drawn into the image data or a corresponding representation. Such markings or specifications may also be taken into account by the data processing device 5 for determining the context, for example, for determining or calculating a spacing of the catheter tip 13 from such a marking and/or for recognizing a deviation of an actual path or an actual position of the catheter 7 or the catheter tip 13 from the pre-defined path.

In the method act S6, therefore, a real and/or meaningful relationship of the respectively represented current situation, for example, of the catheter 7 to a corresponding environment that is, for example, given by the vessel 11, and the stenosis 12 is created or determined. Thus, for example, not only may the spacing 14 be determined as a spacing between two geometrically distinguished points, but the significance of the respective points is automatically recognized, so that the data processing device 5 therefore automatically determines that the spacing 14 specifically defines the distance between the catheter tip and the stenosis 12.

The image and data processing for this may be carried out by a suitably trained neural network. This may classify different objects (e.g., by processing the image data), such as the vessel 11, the stenosis 12 and the catheter 7.

In a method act S7, based on the determined context, speech data 15, which is schematically indicated, is generated by the data processing device 5. This speech data 15 describes at least part of the determined context in speech form and is generated from the patient model or from data obtained or determined thereby. Thus, features, subregions, or objects identified, for example, in the patient model may be named with or linked to respective linguistically correct designations. The speech data 15 may thus describe the respective situation using linguistic expressions. The speech data 15 may be, for example, sentences or fragments of sentences that are generated or composed, derived from the determined context, possibly using a pre-defined grammar. In the present case, as such a speech data item 15, for example, the sentence fragment "another 10 mm to the stenosis center point" may be generated, for example, if a movement of a catheter 7 or of the catheter tip 13 in the direction of the stenosis 12 has been recognized as part of the respective current context. If the physician then continues the movement of the catheter 7 in the direction of the stenosis 12, then at a later time point, for example, as a speech data item 15, the sentence fragment "center of the stenosis reached" may be generated. The speech data items 15 therefore represent a particularly clearly comprehensible linguistic description of the respective situation that is of the respective context. In the method act S7, therefore, the context or an abstract representation of the context determined by the data processing is converted by the data processing device 5 into a speech form.

In further exemplary embodiments, the speech data 15 may describe or express, for example, a deviation of the catheter 7 or another medical object or instrument from a pre-determined or planned or ideal path, a deviation from a corresponding speed, a distance from a planned or pre-set appellation, or the like. Similarly, the speech data 15 may be or contain, for example, indications or warnings (e.g., "vessel branching to right in 13 mm"). Such indications regarding vessel branchings may be, for example, in neurosurgical applications where the vessels or vessel branches involved may be particularly fine, particularly advantageous, and helpful for supporting the physician 1.

In a method act S8, the speech data 15 is then output to the medical personnel (e.g., to the physician 1). For this, the speech data 15 may be displayed as text in a second display region 16 of the display device 9. In one embodiment, the speech data 15 may, however, be output or reproduced by a loudspeaker device 17 in acoustic form (e.g., as acoustic speech output). By this, the physician 1 may concentrate, for example, on the respective clinical investigation, is less distracted, and has an additional safeguard. Similarly, other medical personnel may independently prepare themselves in advance using the output speech data 15 for impending procedures, manipulations, and the like since effectively, relevant thoughts typically had by the physician 1 during the procedure are also made audible for the remaining medical personnel. For example, the acoustic speech output by the loudspeaker device 17 enables all the medical personnel to be informed automatically in a particularly simple and timely way.

The speech data 15 may be output not only in the respective operating room but also at another site. The speech data 15 may be output, for example, for teaching purposes or in the context of a consultation of remotely situated specialists (e.g., in an observation room, in a lecture theater, in a vehicle, on a mobile terminal device or the like). The speech data 15 may be transferred more simply and faster to a respective output location than, for example, the image data. In addition, according to the possibilities and the display quality of a respective remote display apparatus or a respective remote display device, the image data may be reliably recognizable or interpretable only with difficulty, whereas the speech data 15 may be correctly output and understood significantly more easily and reliably.

The creation and output of the speech data 15 may, for example, also be advantageous if medical personnel with different qualifications are present and, for example, are involved in the respective medical procedure. Thus, for example, a radiologist and a surgeon may cooperate during the medical procedure, although, for example, both do not have the same experience or the same knowledge in relation to all the steps of the procedure and/or in the interpretation of a purely image-based representation of the image data supplied by the X-ray device 4. Through the output of the speech data 15, the respective situation is conveyed particularly clearly and comprehensibly.

In a method act S9, for example, determined or recognized deviations of the patient 2 from a normal behavior or a normal state may be stored in a deviation database. This deviation database may also be accessed for determining the context and/or for generating or updating the patient model.

The system for supporting the medical personnel or the physician 1 in the described manner includes at least the data processing device 5. The data processing device 5 may include respective interfaces for receiving and/or for transferring data (e.g., for unilateral or bilateral data exchange with the X-ray device 4, the camera 8, the display device 9, and/or the loudspeaker device 17). Similarly, the camera 8, the display device 9, and/or the loudspeaker device 17 may be part of the system.

The system may be configured as a free-standing separate system or device. It is, however, possible to integrate the system into a larger system or another device. Thus, the system (e.g., the data processing device 5) may be integrated, for example, into a data processing apparatus or combined with a data processing apparatus that reconstructs raw data provided by the X-ray device 4 to the image data.

The method acts described are not to be understood strictly as a sequence of chronologically successive processes. Rather, in connection with different method acts, processes or measures may be carried out simultaneously and/or intersect in duration or execution time (e.g., temporally overlap).

The processing of different data and information as described into linguistic information statements may be, for example, but not exclusively, for interventionally supported medical procedures, an advantageous measure or solution for supporting medical personnel and for improving a sequence of the respective procedure.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for supporting medical personnel in a procedure on a patient, the method comprising:
   continuously capturing image data of the patient and of a medical object generated by a medical imaging method;
   generating and continuously updating a digital patient model using the image data;
   continuously tracking a position of the medical object;
   determining a situational, spatial, or situational and spatial context in which the medical object is situated by automatic processing of the image data by an image processing algorithm;
   automatically generating speech data that describes at least part of the determined context in speech form based on the determined situational, spatial, or situational and spatial context from the digital patient model; and
   outputting the speech data to the medical personnel by an acoustic speech output, as text on a display surface, or by the acoustic speech output and as text on the display surface.

2. The method of claim 1, wherein determining the situational, spatial, or situational and spatial context comprises determining a represented subregion of the patient, an anatomical feature of the patient, a spatial-geometric relation between the medical object and at least one environmental detail, or any combination thereof.

3. The method of claim 2, wherein determining the situational, spatial, or situational and spatial context comprises determining a spacing from a pre-determined, automatically recognized, or pre-determined and automatically recognized anatomical feature of the patient in an environment of the medical object.

4. The method of claim 1, wherein determining the situational, spatial, or situational and spatial context comprises automatically comparing the image data, the digital patient model, or the image data and the digital patient model with an anatomical database provided.

5. The method of claim 1, wherein generating the digital patient model, determining the situational, spatial, or situational and spatial context, or generating the digital patient model and determining the situational, spatial, or situational and spatial context comprise using geometrical data describing a location of the patient, an environment of the patient, or the location of the patient and the environment of the patient.

6. The method of claim 5, wherein generating the digital patient model, determining the situational, spatial, or situational and spatial context, or generating the digital patient model and determining the situational, spatial, or situational and spatial context comprise using a relative position of a patient couch, a relative position of a device generating the image data, or the relative position of the patient couch and the relative position of the device generating the image data.

7. The method of claim 1, further comprising spatially capturing, by a three-dimensional (3D) camera, the patient, an environment of the patient, or the patient and the environment of the patient,
wherein generating the digital patient model, determining the situational, spatial, or situational and spatial context, or generating the digital patient model and determining the situational, spatial, or situational and spatial context comprise processing corresponding camera data provided by the 3D camera.

8. The method of claim 1, wherein the medical object is identified by an automatic object recognition algorithm, by an automatic comparison of the image data with an object database provided, or by the automatic object recognition algorithm and by the automatic comparison of the image data with the object database provided, and
wherein generating the digital patient model, determining the situational, spatial, or situational and spatial context, or generating the digital patient model and determining the situational, spatial, or situational and spatial context comprise recalling object data assigned to the identified object from the object database and processing the object data assigned to the identified object.

9. The method of claim 1, wherein the medical object is a catheter, and
wherein the method further comprises automatically determining, by an image processing algorithm, a diameter of a vessel of the patient at a respective current position of the catheter while the catheter is passed through the vessel of the patient.

10. The method of claim 9, wherein automatically determining the diameter of the vessel of the patient at the respective current position of the catheter while the catheter is passed through the vessel of the patient comprises automatically determining the diameter of the vessel of the patient at a respective current position of a tip of the catheter while the catheter is passed through the vessel of the patient.

11. The method of claim 1, wherein continuously capturing image data comprises continuously capturing the image data between two documentation images of the patient, the continuously capturing of the image data between the two documentation images of the patient recorded comprising recording a plurality of fluoroscopic images with reduced radiation intensity, and
wherein continuously updating the digital patient model comprises processing the plurality of fluoroscopic images.

12. The method of claim 1, wherein automatically generating speech data comprises generating different speech data,
wherein the method further comprises classifying the different speech data into different categories dependent upon content relating to an anatomic feature, the medical object, or a spatial, temporal, or spatial and temporal relation, and
wherein outputting the speech data comprises outputting only speech data from selected categories.

13. The method of claim 1, further comprising:
processing, by a method of machine learning, the image data, the patient models, or the image data and the patient models of a plurality of different patients, such that a normal state, a normal behavior, or a normal state and a normal behavior of at least a part of the patient is learned;
automatically recognizing a deviation between the respective current image data, the respective current digital patient model, or the respective current image data and the respective current digital patient model, and the normal state, the normal behavior, or the normal state and the normal behavior; and
generating and outing speech data describing the deviation, storing the respective current image data, the respective current digital patient model, or the respective current image data and the respective current digital patient model in a deviation database.

14. The method of claim 13, wherein the method of machine learning is a neural network.

15. A system for supporting medical personnel in a procedure on a patient, the system comprising
a capture device configured to continuously capture image data of the patient and of a medical object generated by at least one medical imaging method;
a data processor configured to:
continuously update a digital patient model based on the respective current image data;
track a position of the medical object; and
automatically determine a situational, spatial, or situational and spatial context in which the medical object is situated, the automatic determination of the situational, spatial, or situational and spatial context in which the medical object is situated comprising process of the image data by an image processing algorithm;
a speech synthesis device configured to generate speech data based on the determined situational, spatial, or situational and spatial context from the digital patient model, wherein the speech data describes at least part of the context in speech form; and
an output device configured to output the speech data to the medical personnel by an acoustic speech output, as text on a display surface of the output device, or by the acoustic speech output and as text on a display surface of the output device.

* * * * *